United States Patent [19]

Kaufman

[11] Patent Number: 4,601,286

[45] Date of Patent: Jul. 22, 1986

[54] ARTICLE FOR THE PROTECTION OF LIVING TISSUES

[76] Inventor: Jack W. Kaufman, 367 Frankel Blvd., Merrick, N.Y. 11556

[21] Appl. No.: 602,602

[22] Filed: Apr. 20, 1984

[51] Int. Cl.[4] .............................................. A61B 19/08

[52] U.S. Cl. ................................ 128/132 D; 128/82.1; 128/156; 604/368

[58] Field of Search ............... 128/132 R, 132 D, 155, 128/82.1, 156, 207.14, 207.15, 303.1, 3, 4; 604/265, 266, 368

[56] References Cited

U.S. PATENT DOCUMENTS

| | | | |
|---|---|---|---|
| 3,220,960 | 11/1965 | Wichterle | 128/156 X |
| 3,520,949 | 7/1970 | Shepherd et al. | 128/156 X |
| 3,566,874 | 3/1971 | Shepherd et al. | 604/265 |
| 3,861,396 | 1/1975 | Vaillancourt et al. | 604/265 X |
| 4,303,066 | 12/1981 | D'Andrea | 128/156 |
| 4,378,796 | 4/1983 | Milhaud | 128/207.15 |
| 4,489,722 | 12/1984 | Ferraro et al. | 128/207.15 |
| 4,520,814 | 6/1985 | Weeks | 128/303.1 |

FOREIGN PATENT DOCUMENTS

| | | | |
|---|---|---|---|
| 0073366 | 5/1983 | Japan | 128/303.1 |

*Primary Examiner*—Dalton L. Truluck
*Attorney, Agent, or Firm*—Seymour G. Bekelnitzky

[57] ABSTRACT

An article for the protection of living tissue from damage due to exposure to lasers or microorganisms comprising A. A hydrogel comprising
   1. at least one water-insoluble hydrophilic polymer and
   2. water and B. If desired, at least one additive selected from the group consisting of medications, colorants and moisturizers.

11 Claims, 3 Drawing Figures

7

16

2

10

15

11

2

12

FIG. 1
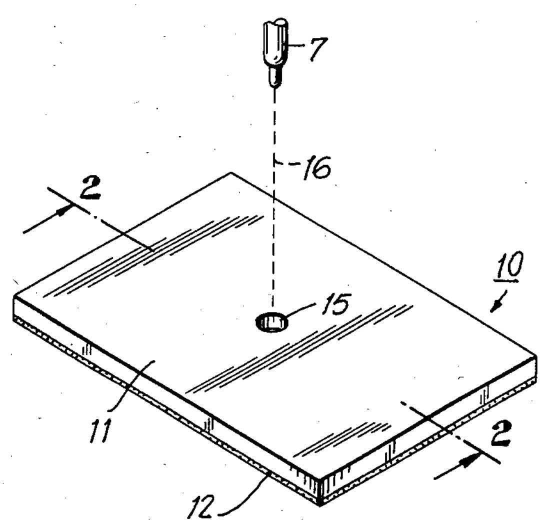
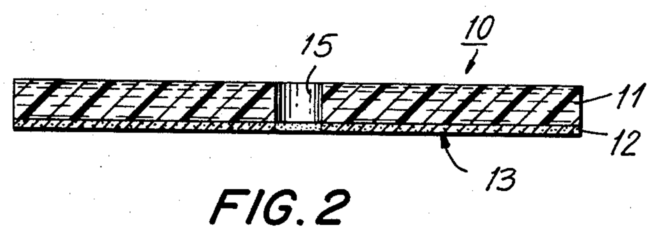
FIG. 2
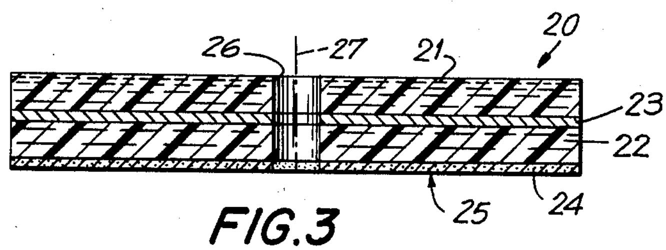
FIG. 3

ARTICLE FOR THE PROTECTION OF LIVING TISSUES

BACKGROUND OF THE INVENTION

This invention relates to articles for the protection of living tissues. More particularly, it relates to articles which are useful in the protection of living tissues from attack by harmful agents such as lasers and microorganisms, said articles being comprised of hydrogels and, if desired, additional additives such as salts, colorants and medications.

Lasers have recently made a significant breakthrough as a preferred, in some, and the *only* modality, in other surgical areas. These areas of increasing use of lasers in surgery and other treatments include, e.g., otolaryngology, gynecology and ophthalmology.

Amongst the main advantages of lasers, in surgery, are their ability to incise and/or remove precisely controlled areas of tissue while permitting visual assessment of the procedure through use of an operating microscope. This visual assessment is facilitated by reduction of bleeding and absence of other instrumentation, which might block the surgeon's view, in laser surgery when compared to conventional surgical techniques.

Furthermore, if the blood vessels are sufficiently small they are sealed, by the laser, after incision. If some bleeding were to occur, for instance, in the case of larger blood vessels it can be efficiently stopped by coagulation using a defocused beam, the defocusing being accomplished by partial retraction of the focusing tip, i.e., by increasing the working distance of the laser beam.

Additional advantages of using lasers in surgery are the limitation of the area of undesireable tissue destruction and the zone of devitalized tissue, fewer post-operative complications and less post-operative pain and scar formation which might hinder healing. As a consequence hospitalization time is reduced.

Nevertheless, the use of lasers, in medical treatments and surgery, is not without disadvantages and hazards, chief among which are the danger of fire and the destruction of viable tissue on the margins, or periphery, of the operative site.

As a consequence normal drape procedures commonly used in laser surgery and treatment are of limited value and potentially dangerous. For instance, a fire hazard is especially present when wet Cottonoids (cotton gauze pads wet with saline) which are used to protect the surrounding tissues and organs from exposure to extraneous laser beams, whether direct or reflected, dry out and ignite due to the high inflammability of dry cotton or cellulosics. This is an always present danger due to the high levels of energy associated with laser beams. Thus, it is necessary for the surgical team to be constantly aware of that possibility and to keep the gauze moistened at all times.

Yet other problems arise in the use of drapes on compound surfaces, i.e. surfaces that are not smooth but rather have cavities and ridges, whereby the usual drapes do not conform to the surface topography thereby permitting gaps to be formed between the tissue surface and drape. These gaps permit the gathering of gases and/or heat therein which ultimately result in undesirable tissue damage.

An additional aspect of the fire hazard is that the laser beam will burn through most plastics or rubbers of which tubes for insertion into body cavities, e.g., endotracheal tubes, are constructed. Thus, the use of plastic or most rubber endotracheal tubes is contraindicated when surgery employing lasers is contemplated. Therefore red rubber tubing or steel, which are less sensitive to lasers, are used in the construction of endotracheal tubes. However, because endotracheal tubes prepared from such materials lack built-in cuffs, they do not make completely airtight seals with the organ walls. To get around that problem it has been necessary to place a separable cuff over the distal end of the tube which has, therefore, resulted in the addition of a balloon-filling tube, passed through the larynx, to an already crowded lumen.

Another problem, the destruction of viable tissue near the operative site is due to the fact that, during surgery using lasers, it is often impossible to concentrate the laser exactly and exclusively on the surgical site. For instance, the incident beam may have a larger diameter than the surgical site or part of the beam may be dispersed or reflected, although at a lower intensity, to a distance from the surgical site. This results in undesireable destruction of healthy tissue at the periphery of, and/or at a distance from, the surgical site. The damage occurs in the same manner as the surgery is effected, i.e., by ablative removal of the water (about 90%) and organic matter of which the tissue is comprised.

In another aspect, exposed tissue, such as in wounds or at operative sites, is vulnerable to attack by disease-causing microorganisms.

It is, therefore, desireable to protect the vulnerable tissues from attack by extraneous laser beams or disease-causing microorganisms while permitting air and moisture to get to the tissue and facilitate the healing process.

However, when such tissue is protected by the usual type of sterile dressing dessication of the tissue ensues. It has, therefore, been found advantageous to cover such vulnerable tissue with dressings that have been wet with water or aqueous solutions of medications. Here again, the afore-mentioned Cottonoids have been used for construction of the dressings. However, use of these prior art dressings has not been without problems due to their limited absorption of the saline solution, facile dessication and poor structural integrity at high fluid contents, whereby it is possible for the pads to disintegrate and portions thereof to infiltrate the wound.

It has now been found that the articles of the instant invention obviate the above problems thereby providing for enhanced tissue protection during laser-effected surgery and treatments and against microorganism attack on exposed and vulnerable tissue whereby healing of the wounds is facilitated.

BRIEF DESCRIPTION OF THE DRAWINGS

FIG. 1 is a perspective view of one embodiment of a surgical drape according to the instant invention;

FIG. 2 is a sectional view taken along line 2—2 of FIG. 1;

FIG. 3 is a sectional view of another embodiment of the instant invention.

SUMMARY OF THE INVENTION

Accordingly, it is an object of this invention to provide articles for the protection of living tissue from damage.

It is a further object of the invention to provide for the protection of living tissue from damage due to attack thereon by microorganisms.

It is yet another object of the invention to provide an article for the protection of living tissue for damage due to exposure to laser beams during treatment or surgery using lasers.

Another object of the invention is to provide a tube, for insertion into body cavities, which is relatively impervious to laser beams yet can maintain airtight contact with the organ walls without requiring a separable cuff and balloon-filling tube.

Another object is to provide a surgical drape which conforms to the tissue topography thereby precluding the existence of gaps between the tissue surface and the drape.

It is yet another object of the invention to provide an article for the prevention of damage to living tissue while keeping the tissue wet with water or, if desired, aqueous solutions of medications.

These and other objects of the invention will be in part discussed and in part apparent upon consideration of the detailed description of the preferred embodiment.

DETAILED DESCRIPTION OF THE PREFERRED EMBODIMENT

In accordance with the invention it has now been found that living tissue may be protected from damage due to exposure to laser beams or attack by microorganisms through the use of articles comprising hydrogels and, if desired, medications.

Thus, in accordance with this invention there is provided an article for the protection of living tissue from damage comprising A. A hydrogel comprising
   1. At least one water-insoluble polymer and
   2. Water and B. If desired, at least one additive such as a medication, colorant or moisturizer.

The hydrophilic polymers useful in accordance with the invention are those which are inherently water-insoluble and those which may be rendered so by crosslinking.

Examples of inherently water-insoluble hydrophilic polymers include copolymers of hydrophobic monomers, such as acrylonitrile, acrylates, (e.g., methyl and ethyl) methacrylates, (such as methyl and propyl) and styrene with hydrophylic monomers such as, acrylamide and acrylic and methacrylic acids. Other inherently water-insoluble hydrophylic polymers may be exemplified by hydrophobic polymers such as silicone, acrylate, methacrylate and urethane polymers whose surfaces have been rendered hydrophylic by treatments such as partial hydrolysis of e.g., ester and amide groups and by grafting of hydrophylic monomers or other functional groups to the hydrophobic backbones.

The inherently water-insoluble hydrophylic polymers useful in the practice of the instant invention include the acrylonitrile-acrylamide copolymers described in U.S. Pat. No. 4,331,783 (issued May 25, 1982) and the modified acrylonitrile-acrylamide copolymers described in U.S. Pat. No. 4,337,327 (issued June 29, 1982), both patents being incorporated herein for reference.

Other polymers of this nature include block copolymers of poly(ethylene oxide) and relatively hydrophobic materials such as polyurethanes which are described, e.g., by E. W. Merrill and E. W. Salzman in their article "Poly(ethylene oxide) as a Biomaterial" (Am. Soc. for Artificial Internal Organs Journal, April/June 1983, pp. 60–64). Such materials are exemplified by Polyox™, a cross-linked poly(ethylene oxide).

Water-soluble polymers which may be rendered insoluble by crosslinking include polymers of hydrophylic monomers such as those mentioned above, hydroxyalkyl acrylates and methacrylates and alkylene oxides such as those of ethylene and propylene. Such crosslinked hydrogels are described in, e.g., U.S. Pat. No. 3,320,960 (issued Nov. 30, 1985) and U.S. Pat. No. Re. 27,401 June 20, 1972.

The particular choice of water-insoluble hydrophylic polymers for use in the articles according to the invention will depend on, e.g., the $pK_a$ thereof and any other factors which could affect biocompatability with the specific body part in contact with the protective article.

Crosslinking may be effected by addition of crosslinking compositions, such as those which decompose into free radicals and polyfunctional materials; by exposure to radiation and by other means known to those skilled in the art.

Examples of compositions which decompose to form free radicals are azonitriles, such as azobis(isobutyronitrile); peroxides, such as benzoyl peroxide; and hydroperoxides, such as cumene hydroperoxide.

Polyfunctional materials useful in crosslinking hydrophylic polymers include the acrylates and methacrylates of polyhydric compounds such as diols, e.g., ethylene glycol; triols, such as glycerol and 1,1,1-tris(hydroxymethyl)propane; tetraols, e.g., pentaerythritol and polyhydric polymers such as epoxy resins. Other crosslinking agents which may be used in the practice of the invention, as well known in the art, include zinc oxide, organotin compounds, N,N'methylenebisacrylamide and diallylidene pentaerythritol.

Radiation-induced crosslinking may be effected by actinic radiation such as UV and visible light; -radiation; and electron beams.

As the sources of laser light provide light of varying wavelengths (e.g., the $CO_2$ laser at 10.6, the Argon laser at 0.48 [i.e., in the blue region of the spectrum] and the ruby laser in the red region at 0.69) it is often necessary to add colorants to the hydrogel to prevent transmission of the laser beams therethrough. Added colorants are not needed only in the case of the $CO_2$ laser, whose light is strongly absorbed by water and, therefore, all tissues. Again the particular crosslinking method must be such as will yield a product which will not depolymerize or decompose, to products which are water-soluble, when exposed to the body environment in which they are used or the operating media.

The protective article may be of any shape or form known in the art such as, dressings, fiber optic tubes, surgical drapes and the like. The particular form to be used at any one time would depend upon the requirements of the user.

According to another embodiment of the invention there is provided an article to protect, and prevent inflammation in, healthy tissue, e.g., around and in a wound, comprising a wet dressing comprising one of the hydrogels described above.

In accordance with yet another embodiment of the invention there is provided an tube for use in laser surgery or treatment, comprising any of the afore-mentioned water-insoluble hydrophylic, polymers which is on its inner surface plated to a mirror finish which will reflect any extraneous laser beams incident thereon. (Of course, in the case where the polymers are not initially water-insoluble crosslinking must occur concurrently with, or after, the extrusion process.) Any beams which pass through said inner surface are absorbed in the tube walls and the energy thereof dissipated. Another aspect of the above embodiment provides for such a tube which is filled with a silver halide material as transmitter of the laser beam. The silver halides useful in the practice of the invention are well known in the art and will not be discussed further.

According to yet another aspect of the above embodiment there is provided a surgical drape, for the protection of healthy tissue from damage due to exposure to lasers during treatment and surgery, comprising a sheet comprising any of the above-indicated hydrogels having a hole cut through the center thereof, of about the same dimensions as the site of tissue exposure to permit unimpeded passage of the beam therethrough and access to only the site to be lased. Perferably the drape will be made to adhere and conform to the topography of the site to preclude oclusion of gases and/or heat which might damage the tissue.

According to yet another embodiment of the invention there is provided a method of protection for healthy tissue in and around a wound from damage due to attack by microorganisms and dessication comprising the steps of (1) applying to the area of such tissue, to be protected, a dressing comprising
  A. a hydrogel comprising
    1. at least one hydrophylic polymer and
    2. water and
  B. if desired, at least one additive such as medications, colorants and moisturizers; and
(2) as necessary, adding to said dressing water or an aqueous solution of the additive, to replace water lost during the time the dressing is in contact with the tissue.

The hydrophylic polymers useful in accordance with this embodiment of the invention may be selected from any of those discussed above.

Another embodiment of the invention provides a method of protecting healthy tissue from damage caused by stray laser beams during treatment with lasers or laser surgery and comprises the steps of (1) applying to the area of, said tissue, to be protected an article comprising
  A. a hydrogel comprising
    1. at least one hydrophylic polymer and
    2. water and
  B. if desired, at least one additive such as moisturizers, colorants and medications.

According to this embodiment the article, may be in the form of, for instance, a dressing having an opening through which the laser light can pass to impinge on the portion of the tissue to be lased said, opening having a size and shape approximating that of the tissue site to be lased.

According to another aspect of this embodiment there is provided an article comprising two layers of any of the aforementioned hydrogels having a layer comprising a metallic sheet interspersed therebetween and in contact with the inner surfaces thereof thereby enhancing the barrier properties thereof. I.e., the laser barrier properties of such a protective article are greater than expected from simply adding the barrier properties of the two separate hydrogel layers and the metallic sheet.

The metal sheets useful in accordance with this embodiment are selected from the group comprising aluminum, gold, titanium, silver, their alloys, and the like. Preferred metals for use in accordance with the invention are aluminum and gold.

As necessary, water or aqueous solutions of additives may be added to the protective article to replace any water which may have been lost during the treatment.

It is believed, although the theory is not essential to the practice of the invention, that the article protects the covered portions of the tissue by absorption of the energy of the laser beam incident thereon in the contained water which dissipates the absorbed energy by evaporation. A portion of the energy is also believed dissipated by scission of the organic portion of the article and ablation thereof.

In yet another embodiment of the invention there is provided a method of applying laser light to a desired tissue site, for treatment or surgery, by transmission of said light through a tubal instrument (e.g., a fiber optic) which focuses said light on the operative site and does not permit escape of extraneous reflected or dispersed light to the atmosphere said tube comprising A. A hydrogel comprising
  1. At least one water-insoluble polymer and
  2. Water and
B. If desired, at least one additive such as a medication, colorant or moisturizer.

The hydrogels and additives useful in the practice of this embodiment of the invention may be selected from those described above.

Such instruments include tubes which must be inserted into body cavities, such as endotracheal tubes, and normally require separable cuffs with balloon-filling tubes. According to this aspect of the invention the need for such appurtenances is obviated by the fact that the hydrogel expands perpendicularly to its lengthwise axis to make airtight contact with the organ walls.

In the practice of this aspect of the invention the protective article may be applied to the tube by coextrusion therewith or by placing a tube comprising the hydrogel around or within the light transmitting tube. It is preferred that the protective material be used as a sheath on the outside of the transmitting tube. The hydrogel comprising tube may be caused to adhere to the light transmitting tube by means of separate adhesives or through its own adhesive properties.

In a preferred aspect the protective material is applied to the transmitting tube as a tape whose inner surface, which will be in contact with outer surface of transmitting tube, is tacky and self-adhesive.

In accordance with another aspect of this embodiment of the invention the light transmitting tube comprises a hollow tube, of the afore-mentioned hydrogel, plated on its inner surface to a mirror finish which will reflect most of the extraneous laser beams incident thereof and absorb the energy of any beams not reflected.

If desired, the above tube may be filled with a silver halide as a transmitting medium. Silver halides for use in accordance with the invention are well known in the art and will not be discussed further.

In FIGS. 1 and 2 there is shown a surgical drape 10 according to one embodiment of the invention. Drape 10 comprises a hydrogel layer 11 wherein the hydrogel comprises at least one water-insoluble hydrophilic polymer and water. An adhesive layer 12 is provided on the surface of layer 11 opposite to the one facing the laser source 7 to provide adhesion to the body tissue upon contact therewith. A hole 15 is provided through layers 11 and 12 to permit the passage of the laser beam 16 from the source 7 to the surgical side disposed below said hole.

Another embodiment of the invention is shown in FIG. 3 wherein there drape 20 is formed of two hydrogel layers 21 and 22 having a metallic sheet 23 interposed between and bonded to the inner surfaces of said layers 21 and 22. An adhesive layer 24 is provided on the surface of the drape opposite to the surface facing the laser source to facilitate conforming contact of the drape with the tissue. A hole 26 is provided through layers 21,22 and 24 to permit passage of the laser beam 27 therethrough.

Here again, as required, water or an aqueous solution of the additives may be applied to the protective article to replace any water lost during the treatment, e.g., by ablation due to the laser energy absorbed and/or evaporation to the environment.

Methods for preparing the articles of the invention are known to the art and will not be discussed further.

The following examples illustrate but do not limit the scope of the invention which is defined by the claims.

EXAMPLE 1

Preparation of a laser fiber optic

A cylindrical tube, having two openings, comprising a copolymer of acrylonitrile and acrylamide was plated on its inner surface to a mirror finish. At one opening, the distal end (i,e., the end furthest from the laser light source), there was inserted a focusing lens for the laser. The tube was then completely hydrated with a normal saline solution to yield a laser fiber optic tube comprising a hydrogel.

A $CO_2$ laser beam was passed through the fiber optic tube from its non-distal to its distal end where it was focused by the focusing lens therein and, thence, transmitted as a narrow, parallel laser beam.

It was found that the tube did not dry out or burn throughout its length.

EXAMPLE 2

Example 1 was repeated except that the tube was packed with a silver halide as the laser transmitting core. Similar results were obtained.

EXAMPLE 3

Example 1 was repeated except that a porous Teflon TM tube was coextruded on the outer surface of and with the acrylonitrile-acrylamide copolymer tube. The copolymer tube was then saturated with a normal saline solution to form the hydrogel. During use of the fiber optic saline or water was added to the hydrogel, as needed, by diffusion through the Teflon tubing whereby the water content and temperature of the fiber optic was maintained constant. Similar results were obtained.

EXAMPLE 4

A sheet of acrylonitrile-acrylamide copolymer, (HYPAN TM, manufactured by S.K.Y. POLYMERS L.P., of Princeton, NJ) was saturated with a normal saline solution.

Said sheet was then exposed to a 15 watt $CO_2$ laser beam at a distance of 10 cm. from the focusing lens.

It was found that none of the laser energy was transmitted through the sheet and its temperature did not rise during the course of the experiment.

EXAMPLE 5

Example 4 was repeated except that distance of the sheet from the focusing lens was 4 cm. Similar results were obtained.

EXAMPLE 6

Example 4 was repeated except that a hole of 0.5 g cm. diameter was made at the center of the hydrogel sheet. The laser beam, with a spot size of radius 0.2 cm. at a distance of 8 cm. from the focusing lens, was aimed through the hole with its axis coaxial with the center of the hole.

It was found that the portion of the beam falling within the area represented by the diameter of the hole was totally transmitted whereas any portion of the beam outside of that area was totally absorbed by the hydrogel sheet with no noticeable rise in the temperature thereof.

EXAMPLE 7

Example 6 was repeated except that the distance of the sheet from the focusing lens was 4 cm. Similar results were obtained.

EXAMPLE 8

Example 5 was repeated except that a film of Polyox TM (Nepera, Inc., Harriman, NY) was substituted for the film of acrylonitrile-acrylamide copolymer. Similar results were obtained.

EXAMPLE 9

Example 7 was repeated except that a sheet of Polyox was substituted for the acrylonitrile-acrylamide copolymer. Similar results were obtained.

EXAMPLE 10

Example 8 was repeated except that a sheet of aluminum foil was inserted between two films of Polyox. Similar results were obtained.

EXAMPLE 11

An acrylonitrile-acrylamide copolymer tube similar to that of Example 1 was placed around a rubber endotracheal tube. The copolymer tube was then completely saturated with normal saline solution whereby it was caused to expand in a direction perpendicular to its lengthwise axis. No expansion took place in the lengthwise direction of the hydrated tube.

When the copolymer covered endotracheal tube was placed in another tube of greater inner diameter, before hydration, it was found that after hydration an airtight seal was formed between the outer surface of the copolymer tube and the inner surface of the outermost tube without the necessity of an additional balloon cuff on the endotracheal tube and a filling tube to effect its expansion thereby cluttering an already crowded lumen.

EXAMPLE 12

Example 11 was repeated except that the acrylonitrile-acrylamide copolymer tube was replaced by a poly(ethylene oxide) tube. The poly(ethylene oxide)

tube was formed by winding a Polyox tape, whose inner surface was tacky, onto the rubber tube and curing the composite to cause adhesion of the Polyox to the rubber. Similar results were obtained.

EXAMPLE 13

Example 10 was repeated except that the aluminum foil was replaced by a gold foil. Similar results were obtained.

EXAMPLE 14

Example 10 was repeated except that the aluminum foil was replaced by a titanium foil. Similar results were obtained.

I claim:

1. A surgical drape for the protection of healthy tissue from damage due to undesired exposure to lasers during surgery comprising a sheet having a hole therethrough, said hole having about the same dimensions as the site of tissue exposure to permit unimpeded passage of the beam therethrough and access to only the site to be lased said drape comprising a hydrogel comprising A. at least one hydrophilic water-insoluble polymer and B. water.

2. The drape according to claim 1 further comprising at least one additive selected from the group consisting of pharmaceutically acceptable salts, colorants and medications.

3. The drape according to claim 1 wherein the hydrophilic water-insoluble polymer comprises an acrylonitrile-acrylamide copolymer.

4. The drape according to claim 3 wherein said drape comprises two layers of hydrogel having a layer of metallic sheet interspersed therebetween and in contact with the inner surfaces thereof.

5. The drape according to claim 1 wherein the hydrophilic water-insoluble polymer comprises a crosslinked poly(ethylene oxide).

6. The drape according to claim 5 wherein said film comprises two layers of hydrogel having a layer of metallic sheet interspersed therebetween and in contact with the inner surfaces thereof.

7. A method for protecting healthy tissue from damage due to undesired exposure to lasers during surgery comprising the steps of (1) applying thereto a surgical drape comprising a sheet having a hole therethrough, said hole having about the same dimensions at the site of tissue exposure to permit the unimpeded passage of the laser beam therethrough and access to only the site to be lased said sheet comprising a hydrogel comprising A. at least one hydrophilic water-insoluble polymer, B. water, and C. if desired, at least one additive selected from the group consisting of medications, colorants and moistureizers; and (2) as necessary, adding to said drape water or an aqueous solution of additive, if any, to replace water lost during the time the drape is in contact with the tissue.

8. The method according to claim 7 wherein the water-insoluble polymer comprises an acrylonitrile-acrylamide copolymer.

9. The method according to claim 7 wherein the water-insoluble polymer comprises a crosslinked poly(ethylene oxide).

10. The method according to claim 7 wherein said drape conforms and adheres to said tissue either self-adhesively or by means of an adhesive interposed between said dressing and said tissue surface.

11. The method according to claim 10 wherein the inner surface of said drape is tacky whereby said dressing adheres to said surface self-adhesively.

* * * * *